United States Patent
Rehak et al.

[11] Patent Number: 5,951,555
[45] Date of Patent: Sep. 14, 1999

[54] DEVICE FOR THE CORRECTION OF SPINAL DEFORMITIES

[76] Inventors: Lubos Rehak, Bajzova 14, 821 08 Bratislava; Daniel Svrcek, Halova 10, 851 01 Bratislava; Josef Cech, Svatoplukova 43, 821 08 Bratislava, all of Slovakia

[21] Appl. No.: 08/952,766
[22] PCT Filed: Mar. 27, 1996
[86] PCT No.: PCT/SK96/00003
 § 371 Date: Feb. 23, 1998
 § 102(e) Date: Feb. 23, 1998
[87] PCT Pub. No.: WO97/35529
 PCT Pub. Date: Oct. 2, 1997
[51] Int. Cl.⁶ .................................................. A61B 17/70
[52] U.S. Cl. ................................................................ 606/61
[58] Field of Search .................... 606/61, 60, 72, 606/73; 623/17

[56] References Cited

U.S. PATENT DOCUMENTS 5,672,175 9/1997 Martin ....................................... 606/61
5,720,746 2/1998 Soubeiran ................................. 606/61
5,733,284 3/1998 Martin ...................................... 606/61

FOREIGN PATENT DOCUMENTS 654249 5/1995 European Pat. Off. .
677277 10/1995 European Pat. Off. .
WO95/05783 3/1995 WIPO .

*Primary Examiner*—Guy V. Tucker
*Attorney, Agent, or Firm*—Jones & Askew

[57] ABSTRACT

The device consists of at least two segments which are fixed on spinal vertebrae and which are mutually interconnected. Each segment (1) is fixed on at least one vertebra (7) by means of at least one fixing segment (3). Each segment (1) is connected by means of at least one spring (4) by the force coupling with at least one other segment (1') fixed on at least one other vertebra (7'). The connecting line of 8 the spring (4) ends contains with the vertical vertebral axis (7) an angle to 45° in the frontal as well as in the sagittal plane in the ventral and/or dorsal direction. Required stability of the spine is ensured while preserving the necessary flexibility and adaptation to growth.

10 Claims, 5 Drawing Sheets

Fig_2

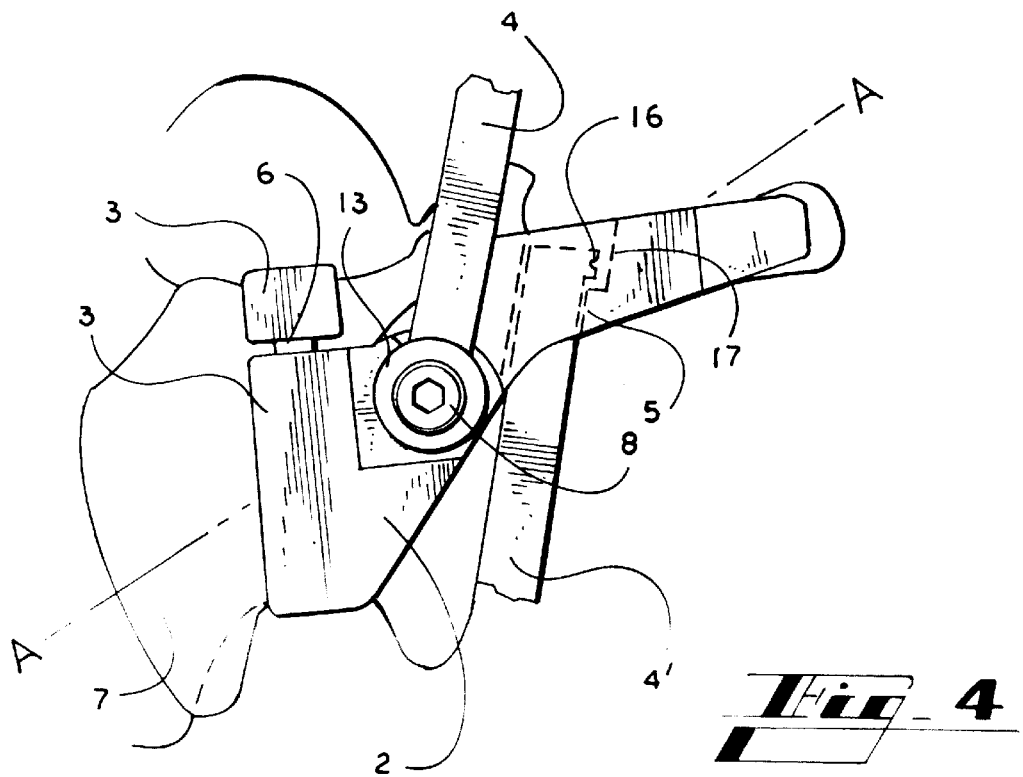
Fig_4
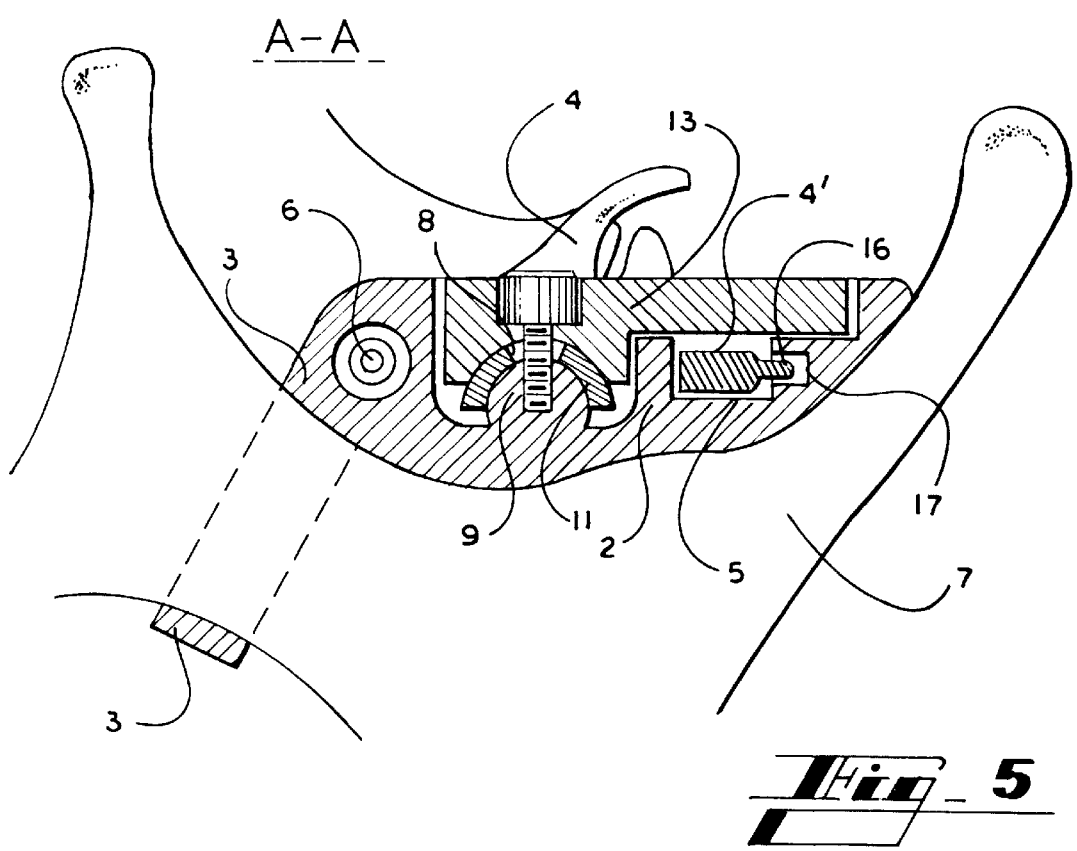
Fig_5

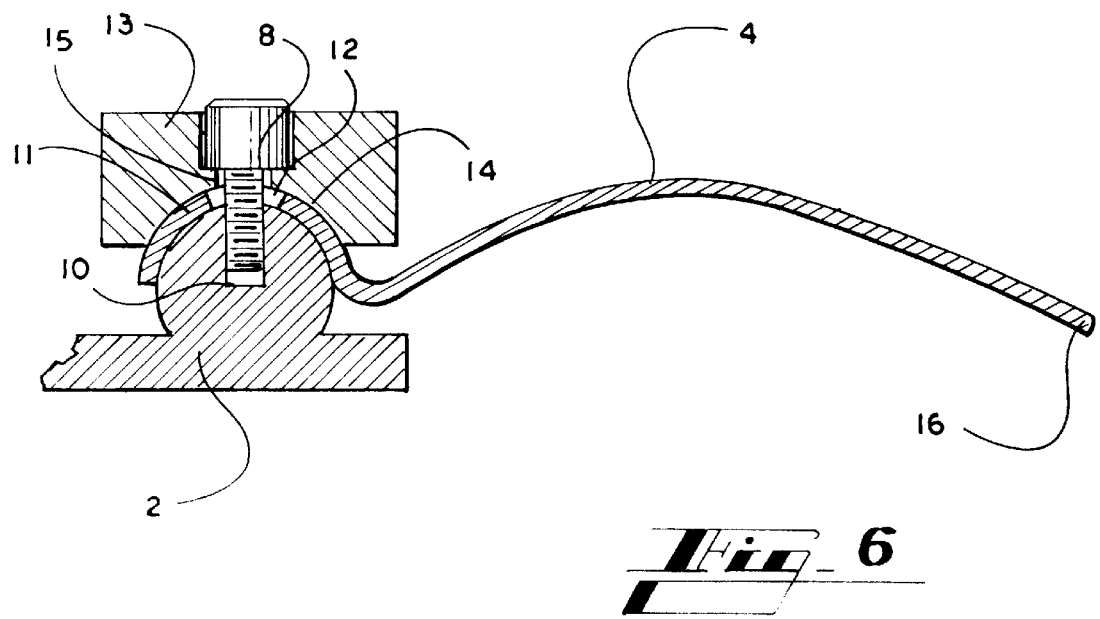
Fig_6
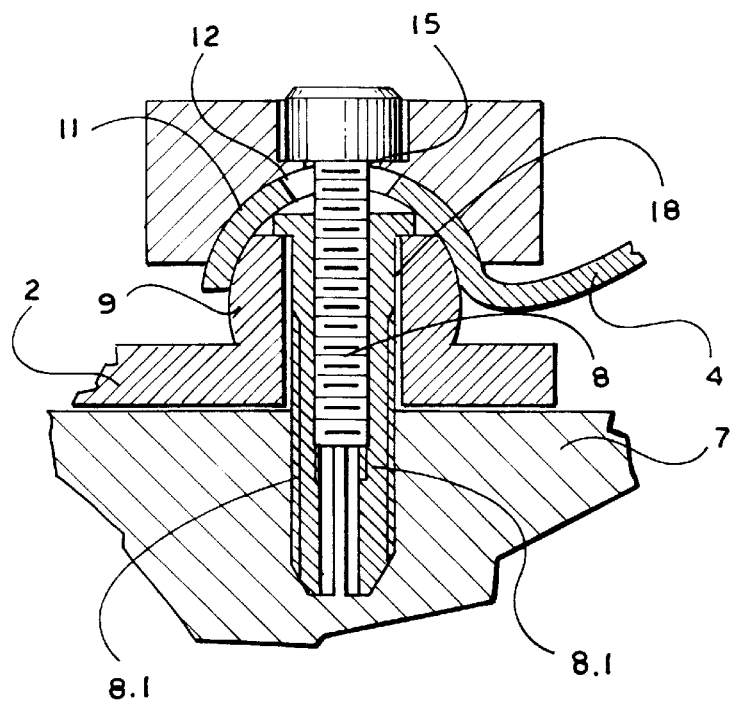
Fig_7

DEVICE FOR THE CORRECTION OF SPINAL DEFORMITIES

This application is filed under 35 U.S.C. 371 based on PCT/SK96/00003, filed Mar. 27, 1996.

TECHNICAL FIELD

The invention relates to the device for the correction of spinal deformities based on metal implants applied by an operation.

BACKGROUND ART

Under the term of the spine deformity are herein understood scolioses (abnormal curvatures of the spine in the sagital plane) and pathological kyphoses and lordoses (abnormal curvatures in the sagital plane). The operative correction of spine deformities by means of metal implants made of special stainless biocompatible steels and titanium alloys, represents the most effective manner of medical treatment of spine deformities and at the same time, a medico-technical problem which is being actual practically already one century, and which still has not been solved with satisfaction. Actually are known several principal constructive solutions for implants to treat spine deformities but each of them has, in addition to certain advantages, also a series of insufficiences. The whole set of known solutions may be divided into three basic groups which may be characterized in the following manner.

The first group represents a set of solutions which may be characterized as rigid systems. A significant feature of these systems is that they contain at least one rod or a plate which is introduced by an operation on the place of a spine deformity, almost in parallel with the spine, while in its whole lenght it is connected with at least two spinal vertebrae by various shaped fixing elements (hooks, clamps, screws, wire knots, etc) installed on it which are fixed on the body or the processus or the laminae of vertebrae. Usually two rods are used which are mutually in at least two spots interconnected and operationally installed along the sides of the spine while several or all vertebrae are then connected with them in its deformity place. From the functional point of view occurs the correction of the deformity by acting, regarding the long spinal axis, of cross tensile and/or pressure forces on deformed vertebrae while is made use of the rigidity of the rod or rods. These systems usually well correct and also stabilize the spine in all three planes but they do not allow the motion and the growth of stabilized segments. Therefore, when applying them, the joints are abolished by an operation and by putting on bone grafts will be evoked that the spine will grow together (spondylodesis, fusion) in the deformity place and that will locally prevent its growth and the mobility will be annulled. Presently, it is possible to insert here as representatives, for instance, of the Wisconsin instrumentations [Drummond D. S., J. Pediatr. Orthop., 4,1984, 397–404; Drummond D. S., The Orthop. Clin. of North Am., 2, 1988, 208–289], Cotrel-Dubousset [Cotrel Y., Dubousset J., Rev. Chir. Orthop., 70, 1984, 489–495; Cotrel Y., Dubousset J., Orthop. Trans., 9, 1985, 118], TSRH, the Isola system using the rod combined with the plate [Asher M. A. et al.: Isola Spine Implant System: Principles and Practice, acroMed, Cleveland, 1991], Central-Stab-System, the Luque instrumentation [Luque E. R., Cardoso A., Orthop. Trans., 1, 1977, 136; Luque E. R.: Tailoring Surgery to Spinal Pathology. In Segmental Spinal Instrumentation. Thorofare, N.J., Slack Co., 1984] and others. This group may include also internal fixators (e.g. Socon (Socon-Fixateur Interne-Aesculap, Prospekt N. C-627 1091 (3, Germany), Kluger's fixator [DE P321957.3; Dick W. et al., Paraplegia, 23, 1985, 225–232], Matzen's fixator [Internal Fixator for the Lumbar Spine acc. to Matzen, Ulrich, Dr. HS (de Apr. 16, 1992 derer/e-matzen.pm.3] and others).

The second group is represented by systems which may be characterized as semirigid ones. For these instrumentations is typical that, they are made of:

a) The rod equipped at least at its ends with appropriately shaped fixing elements, which is by an operation applied from the concave or convex side of the deformity, and the fixing elements are fixed, under the actual maximum possible straightness of the spine deformity, on vertebrae in the area of the beginning and the end of a deformity, while from the functional point of view the correction of a deformity occurs by acting parallel expanding forces with the long spinal axis on its concave side or by acting pressing forces on its convex side;

b) The wind spring equipped at its ends with appropriate fixing elements and which is applied by an operation from the convex side of the deformity, and the fixing elements are at actual tension of the spring fixed on vertebrae in the area of the beginning and the end of the deformity while from the functional point of view the correction of the deformity occurs by acting parallel forces with the long spinal axis on its convex side, c) From the combination of elements according to both previous points which may be also mutually interconnected while from the functional point of view the correction of the spinal deformity occurs by acting parallel compressing forces on its convex side and simultaneously by acting parallel distracting forces on its concave side.

Instrumentations belonging to the group of semirigid systems appropriately correct the spinal deformities and significantly or fully restrict the motion within the area of the spinal deformity only in the direction of acting correction forces. The spine is never corrected in all three planes (therefore, at their application the external fixation by the corset or jacket is always inevitable), but the instrumentations restrict the growth of the spine for at their application the joins are abolished by an operation and the spondylodesis is evoked. This group include, for instance, Allan's [Allan F. G., J. Bone Joint Surgeon, 37(B, 1955, 92–96] and Kazmin's distractor, spiral springs according to Gruca [Gruca A., Beitr. Orthop. u. Traumal., 5, 1958, 1–11; Gruca A., J. Bone Joint Surg., 40(A, 1958, 570–584], their modification according to Weiss [Weiss M., Bentkowsky Z., Clin. Orthop., 1974, 103–109], Harrington's distraction and compression system [Harrington P. R., J. Bone Joint Surg., 44(A, 1962, 591–610; Harrington P. R., Orthop. Clin. of North Am., 3, 1972, 49–67], and others.

The third group may be characterized as telescopic systems which are characterized by the fact that they consist of:

a) The rod of a constant lenght on which are fixed appropriate fixing elements so that the position of at least one element is adjustable in the long spinal axis direction.

b) Two rods (the telescopic rod is made as a rod inserted by one its end into the coaxial tube) mutually interconnected on both ends, with fixing elements usually situated at the ends of rods, while the length of rods, and thus also the position of at least one fixing elements, is adjustable in the long spinal axis direction.

The mentioned instrumentations are applied by an operation along the sides of the spinal deformity and through its fixing elements ensure the transfer of correcting forces on deformed spinal vertebrae. With the instrumentation according to the point a) it is possible, at periodically repeated operative interventions of a local scope, to change every time the position of at least one fixing element so that this position be brought into harmony with the growth of the spine. The instrumentation according to the point b) is spontaneously modified in the length in accordance with the growth of the spine. A significant disadvantage of these instrumentations is the minimalization of the scope of unevitable changes on the spine and the use of one and only once applied instrumentation by an operation for the period of the spinal growth. But, they have still a disadvantage characteristic for all the other, till now not mentioned solutions, i.e. significant restrictions of the spinal mobility. This group may actually include Harrington's distraction instrumentation [Moe J. H., Orthop. Clin. of North Am., 3, 1972, 17–48] using a ratchet or threaded rods which does not assure the rotational stability, and therefore the external fixation of the spine by a corset or jacket is unevitable. The last system is Ulmer-Teleskop-Stab instrumentation used with the neuromuscular scolioses which stabilizes the spine in all three planes (the need of fixation by the corset or jacket is therefore not required), it corrects the deformity and at the same time, it follows telescopically its growth in the direction of its long axis.

From the above-mentioned facts it in obvious that all till present known solutions of devices for correcting spinal deformities have two significant disadvantages:

1) A significant restriction, respectively, the total liquidation of the mobility and growth of the spine at minimum in the area of its deformity,
2) The need to perform multiple operative interventions at their application on the growing spine what means a great load for the patient's organism.

The aim of the submitted invention is to provide the medical practice such an instrumentation which will suppress these insufficiences to a maximum possible extent or which will fully eliminate them.

DISCLOSURE OF INVENTION

The device for correcting the spinal deformities according to the invention consists of at least two segments which are fixed on the spinal vertebrae and which are mutually interconnected while the principle of the invention is that each segment consists of the segment body connected with at least one fixing element (e.g. in the form of the hooks, clamps, screws, wire knots, etc.), by which the segment is fixed on at least one spinal vertebra in the area of its deformity and at the same time, it contains at least one spring the length of which is significatly greater than its other dimensions and by means of which is connected through the power coupling with at least one other segment fixed on at least one other spinal vertebra. Moreover, the line going through the beginning and the end of the spring forms an angle to 45° with the vertical vertebral axis in the frontal as well as in the sagital plane, in the ventral and/or dorsal direction.

The solution according to the invention may include two basic alternatives of fixing the spring. In the first case each end of the spring is firmly fixed (for instance, in such a manner that it is made as an integral part of the segment body or it is fixed on it by the weld, screw joint, etc.) on another segment and thus forms the bridging between them which provides the force transfer from one segment to anther. In the second case one end of the spring is firmly fixed on one segment and the second segment is equipped with the bearing case in the form of the depression or in the form of the aperture in the body of another segment, in which the second end of the spring is stored. The bearing case when applying the device according to the invention, insulates the contacting spot of the spring with the segment from surrounding tissues and thus prevents their damage when moving the free end of the springy element due to the flexion of the spine. The bearing case has principally a form of the ring or a part of the ring with a circular, elliptical or rectangular aperture, respectively, with a circular, elliptical or rectangular aperture, created in the segment body while the cross dimensions of the aperture are at least by 0.01 mm greater than the corresponding dimensions of the springy element free end.

From the production as well as application point of view it is convenient if the segments are unified, i.e., if every segment contains an springy element fixed on it and a bearing case as well. When applying the segments on a spinal deformity is required that the forces acting through segments on individual vertebrae have a differenciated size, i.e. that the springs fixed on separate segments have differenciated mechanical features. It may be conveniently achieved in such a manner that individual springs are made from a different material and/or they have different cross sections in respect to their longitudinal axes and/or they differ in shape and/or they are fixed on separate segments in different positions, from the point of view of the their fixation place on the segment as well as of their slope regarding the vertebral vertical axis.

From the point of view of the unification required at the production of segments and the simplicity of their application on the spine is very important if a prominence is formed on the segment body in the shape of a globular section in which at its top an aperture with the thread is created and the end of the spring is also shaped in the form of a follow globe section having the internal diameter principally equalling to the mentioned prominence radius, but having the height legs by at least 0.01 mm, and in which at its top is created a through circular aperture. In addition to it, the segment contains also a fixation washer with the excavation in the shape of a globular aperture having the diameter principally equal to the external radius of the mentioned end of the spring and near the top of the mentioned excavation is formed a circular aperture, while the mentioned spring end is a concave side placed on the mentioned prominence and on its convex side is located the mentioned excavation of the fixation washer. The mutual position of these elements is fixed by a screw having the diameter less by at least 0.01 mm than the diameter of apertures in the spring and in the fixation washer through which it passes and which is tightened in the thread found near the top of the mentioned prominence on the segment body. The principal advantage of such a construction of the segment is that with a minimum variety of shapes of springs and segments, relative simplicity of their shapes and production and a simple assembly at their application on a spinal vertebra, respectively, vertebrae, it is possible by means of a simple change in turning the spring, within the scope of angles, determined by characteristics of a given deformity and a concrete segment production (mainly related to the mutual ratio of the screw diameter and the aperture size at the end of the spring), to reach a large variety of force acting between separate segments.

In cases, when for the correction of an expressive spinal deformity is required to form a strong force coupling between segments, mainly in the dorsal direction, that there is a real danger of damaging this part of a spinal vertebra on which the segments are fixed, it is extremely important if the segment is made principally in such a manner as described above, but with the difference that in a given spherical prominence on the segment body is created a through aperture leading to at its top. Through this aperture passes a hollow screw which is tightened in a vertebra, most conveniently, through the pedicle in the spinal vertebra body, and in this screw is an aperture with the thread to fix the screw fixing a mutual position of separate parts of the segment. By means of such a constructive solution it is possible to rather better distribute the force load acting on the vertebra in the place of fixing the segment and thus significantly reducing the possibility of its damage.

For both last mentioned alternatives of the constructive execution of the segment it is convenient if the later contains the bearing case in the form from one side open excavation created in the segment body while this bearing case is covered by the fixation washer from its open side. This helps to reach a full insulation of the spring end from the tissues in its surrounding and at the same time, it will significantly simplifies the segment application on spinal vertebrae since after the installation of the first segment with a spring it is possible, without a force coupling, to instal the second segment and the force coupling between the mentioned segments will be formed by an additional insertion of the spring end into the bearing case while its position in the case is fixed by the fixation washer of the second segment as well as by the fixation of its own spring.

While the spring is fixed only on one segment and its free end is inserted into the bearing case of the following segment, due to the limited length of this case there is a real danger that a very big flexion of the spine may evoke the release of the spring free and from the bearing case and the consequent serious damage of surrounding tissues, leading to the necessity of a futher operative intervention. The mentioned danger is eliminated by such a construction of the spring and the bearing case according to the invention, in which the spring contains at its free end at least on a part of its circumference the enlargement, and at the end of the bearing case remoted from the segment, on which the mentioned spring is fixed, on a part of its length is formed a groove into which the free end of the spring will fall at the excessive flexion of the spine. The mentioned groove in the bearing case is approprietary made in such a manner that it allows within a given scope not only the straight-lined notion but also the rotational motion of the spring in the bearing case.

From the point of view of applying the segment on a spinal vertebra it is convenient if the segment contains a fixing element in the form of a shaped clamp equipped at the ends of arms with a fixation screw which allows, when applying the segment on a vertebra, to tightened together the ends of the shaped clamp arms. The aperture in the shaped clamp corresponds to the arch shape of the spinal vertebra on which the segment will be fixed, it conveniently has a shape of the cross cut of the vertebral arch in the place between the spinous processus and the pedicle of the vertebra.

The device for the correction of spinal deformities according to the invention has, in addition to all already mentioned advantages compared with solutions according to the state of technics a very significant advantage that due to the springy interconnection of its individual segments it allows the patient flexions of the spine in a scope required for the normal life and also during the intensive growth of the spine which it does not restrict, and at the same time, the force coupling between segments is so firm that any orthosis is needed. The submitted solution is so constructively as well as applicably flexible and it may be very simply modified to a concrete kind of the spinal deformity and due to the limited number of required operative interventions (usually one or two operations will be sufficient) it represents for the organism of the patient a minimum load at shortening the time for the operation and decreasing the blood losses.

BRIEF DESCRIPTION OF DRAWINGS

For a better comprehension of the invention the solution is shown on the enclosed drawing where it represents:

FIG. 4 A view on a segment with a shaped clamp and a partial cut of the bearing case.

FIG. 5 A cross cut of the A—A segment according to the FIG. 4.

FIG. 6 A cross cut of the spring with a fixation washer and a screw.

FIG. 7 A cross cut of a segment fixed on the vertebra by a hollow screw.

MODES FOR CARRYING OUT THE INVENTION

EXAMPLE 1

Figure 1:
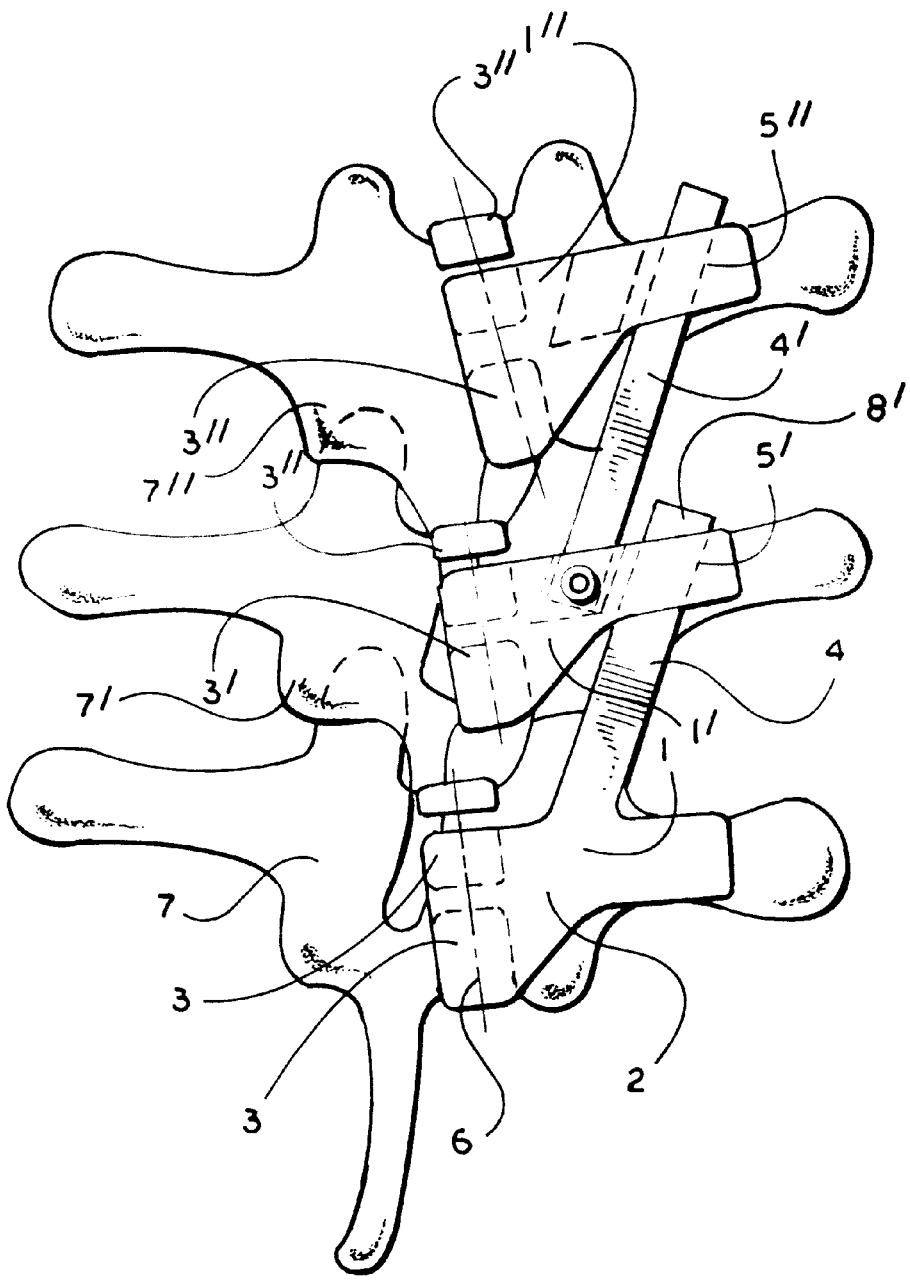
FIG. 1 A schematic view on three segments situated on three spinal vertebrae.

Segments 1, 1' and 1" according to the FIG. 1 are made of stainless steel according to the ISO 5832/211 while the segment 1 fixed on the vertebra 7 consists of the segment body 2 and a fixing element 3 made as a shaped clamp, the arms of which are mutually tightened together by a tightening screw 6. An integral part of the segment body 2 is a spring 4, the second end of which is located in a bearing case 5' of the next segment 1', which is made as a through aperture. The next segments 1', 1" are equipped with identical fixing elements 3', 3" made as a shaped clamp while each of the mentioned segments 1, 1' is constructively modified for fixing on one spinal vertebra 7', 7". When applying the device for the correction of spinal deformities according to the FIG. 1 the segment 1 is firstly fixed can the vertebra 7 by means of its fixing element 3, at the end of its spring 4 is inserted the bearing case 5' of the segment 1' which is turned by appropriate instruments to a position ensuring the creation of a required force coupling between the segments 1 and 1' and by means of its fixing element 1" is fixed on the spinal vertebra 7". The third segment 1" is fixed on the spinal vertebra 7" by its fixing element 3" and then by means of appropriate instruments is turned to a position required for the creation of necessary force acting on the segment 1', in this position the spring 4' will be transplaced through its bearing case 5" and its and is fixed on the segment 1' by the screw 8'.

EXAMPLE 2

Figure 2:
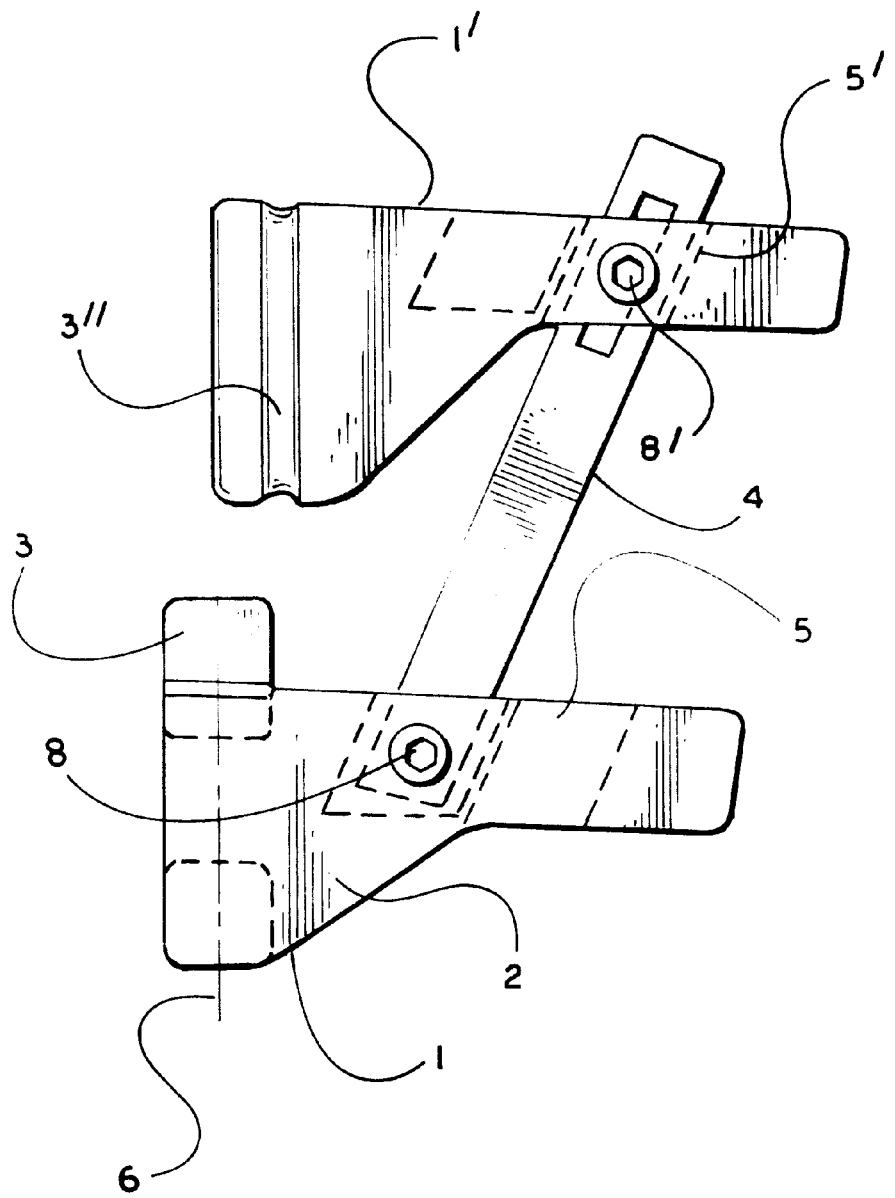
FIG. 2 A view on two segments interconnected with one spring firmly fixed on both segments.

The segments 1, 1' according to the FIG. 2 are made of stainless steel according to the ISO 5832/211, while the segment 1 containts the fixing element 3 made as a hook. In the body 2 of the segment 1 is inserted and by the screw 8 fixed the spring 4 the second end of which is firmly fixed by the screw 8 in the bearing case 5' of the next segment 1', which is made as a through aperture. In the spring 4 is created at its end a longitudinal aperture, through which passes the screw 8' and by means of which, during the growth of the spine may be modified the distance between both mentioned segments. The second segment 1' is equipped with the fixing element 3' made as a groove on the surface of the fixing element 3' into which, when applying the segment on the spine, is inserted a wire knot fixing the element on a corresponding vertebra. Each of the mentioned segments 1, 1' is constructively modified for being fixed only on one spinal vertebra.

EXAMPLE 3

Figure 3:
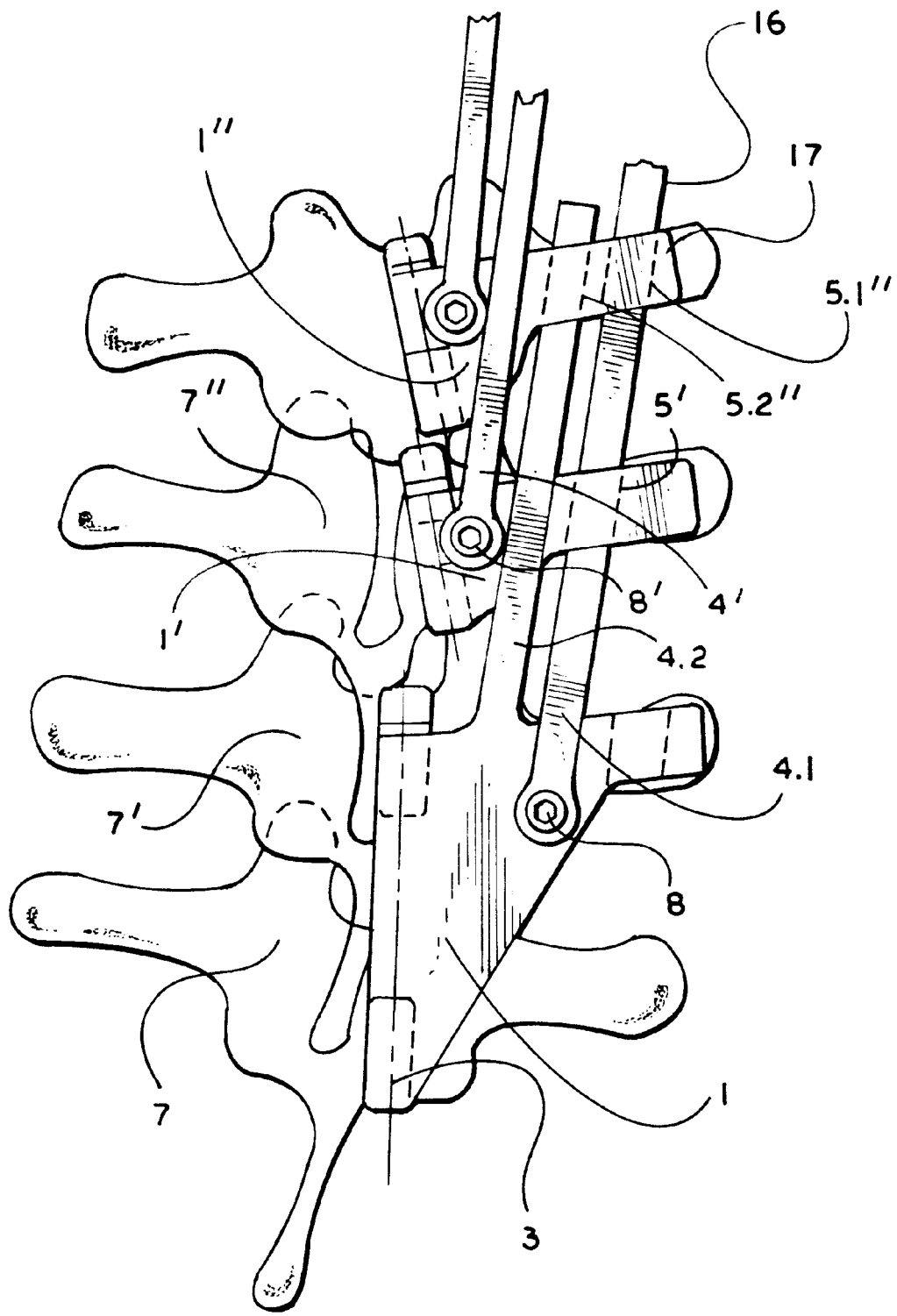
FIG. 3 A schematic view on three segments with marked spinal vertebrae on which they are fixed.

The device for correcting the spinal deformities according to the FIG. 3 is made from the titanium alloy Ti—6Al—7Nb and consists of three segments 1, 1', 1" from which only the first segment 1 is fixed on two spinal vertebrae 7, 7' by means of the shaped clamp 3 and the other are in the same way fixed always on one vertebra. On the segment 1 are fixed two springs 4.1, 4.2 from which the first spring 4.1 has long its entire length a constant rectangular cut and is made of stainless steel according to the ISO 5832/1 and is fixed on the segment 1 by the screw 8 while it goes through the bearing case 5', made as a rectangular excavation in the second segment 1', and the bearing case 5.1" made also as a rectangular excavation in the third segment 1", in which the made groove 17 prevents the declutching of the spring 4.1, equipped at one end with the prominence 16 of the case 5.1". The second spring 4.2 is an integral part of the segment 1, has along its entire length a constant circular cut and is fixed with its second end in the second bearing case 5.2" of the third segment 1", made as a through aperture of the circular cut.

EXAMPLE 4

A segment of the device for the correction of spinal deformities according to the FIG. 4 and consists of the fixing element 3 made as a shaped clamp and the body of the segment 2 on which the prominence 9 is formed in the shape of a globular section (see the cut A—A in the FIG. 5) with the aperture 10 and the thread. On the prominence 9 is stored an equally shaped end 11 of the spring 4 with the through aperture 12 (for more details see the FIG. 6) and the fixation washer 13 is put on it, equipped with a semi-circular excavation 14 and a through aperture 15 at its top while the mutual position of the mentioned elements is fixed by the screw 8, passing through the mentioned apertures 12, 15 and being tightened in the aperture 10 having the thread. The bearing case 5 is made as a from one side open excavation in the body 2 of the segment in which on one side, in about the mid of its length, a groove 17 is made. In the case 5 is located a free end of the spring 4', firmly fixed on the not shown previous segment equipped at one end with the prominence 16 which is situated in the groove 17. The position stability of one end of the spring 4' in the bearing case 5 is ensured by the fixation washer 13 which loses the open side of the bearing case 5. The spring 4' is fixed on the previous not shown segment in such a position that under the pressure it touches the body of thee segment 2 and pushes it to the position ensuring the correction of a given spinal deformity.

EXAMPLE 5

A segment of the device for the correction of spinal deformities according to the Example 4 but differentiated for it contains (see the FIG. 6) the spring 4 fixed on the body of the segment 2 which is not straight-lined, but which is shaped along its entire length in such a manner that, at also limited opportunities for changing its position regarding the body 2 of the segment, it is possible to reach, due to its curvature, a required force acting on the next vertebra.

EXAMPLE 6

A segment of the device for the correction of spinal deformities according to the Example 5 but differentiated in such a way that in the prominence 9 a through aperture 16 is formed (see the FIG. 7) in which a hollow screw 8.1 ok is located. The mentioned hollow screw 8.1 is equipped on its external surface with a thread and it has in its interior an aperture 10 with a thread, while one end screwed in the vertebra 7 is divided by longitudinal cuts on at least two parts. In the aperture 10 with the thread the fixation screw 8 is located which when being screwed into the aperture 10 having the thread spreads separate longitudinal parts of the hollow screw 8.1 and thus increases the strength of its fixation in the vertebra 7.

The above-mentioned examples of the device for the correction of spinal deformities according to the invention represents wanly illustratively concrete executions which in any case do not restrict the extent of the invention defined in patent claims.

INDUSTRIAL APPLICABILITY

The device according to the invention may be appropriately applied, due to its constructive modification, to all known spinal deformities.

We claim:

1. The device for the correction of spinal deformities, comprising:

at least two segments adapted for affixation on spinal vertebrae and which are mutually interconnected;

each segment (1) comprising a body (2) of the segment equipped with at least one fixing element (3) adapted for affixation on at least one spinal vertebra (7) and with at least one spring (4), by means of which a first segment is connected by force coupling with at least one other segment (1'); and the spring (4) having ends disposed on a connecting line that forms a 45° angle with the vertical vertebral axis (7) in the frontal plane and a 45° angle in the sagittal plane in either the ventral or dorsal direction.

2. The device according to claim (1), wherein a first end of the spring (4) is firmly connected with one segment (1) and a second end of the spring is firmly connected with the other segment (1').

3. The device according to claim 1, wherein a first end of the spring (4) is firmly fixed on one segment (1) and a second segment (1') is equipped with a bearing case (5) in the form of an aperture in the body (2') of the segment in which the second end of the spring (4) is received, and the cross dimensions of the aperture are greater by at least 0.01 mm than the corresponding dimensions of the second end of the spring (4).

4. The device according to claim 3, wherein each segment (1, 1') contains at least one spring (4) and one bearing case (5).

5. The device according to claim 1 wherein the segments (1) are adapted for being applied on different places of a spinal deformity, and the springs (4) differ from each other in at least one of their dimensions or the material they are made of or in the shape or the angle which they form with the vertical vertebral axis (7).

6. The device according to claim 3, wherein:

on the segment body (2) a prominence (9) is formed having the shape of a globular section in which near its top a threaded aperture (10) is located;

an end (11) of the spring (4) has a form of a hollow globe section of an internal diameter, substantially equal to the prominence (9) radius but of height smaller by at least 0.01 mm;

a through circular aperture (12) is formed near the top of the globe section so the segment (1) contains a fixation washer (13) with an excavation (14) having the form of a globular section of a diameter substantially equal to the external radius of the end (11) of the spring (4);

a through aperture (15) is formed near the top of the excavation (14);

the end (11) of the spring (4) is by its concave side of the hollow globe section disposed on the prominence (9);

the convex side of the hollow globe section is disposed on the excavation (14) of the fixation washer (13); and the mutual position of these elements is fixed by a screw (8) having a diameter less by at least 0.01 mm than the diameter of the apertures (12, 15) through which the screw passes and is screwed in the threaded aperture (10).

7. The device according to claim 6, wherein:

in the prominence (9) of the globular section form, near its top, is created a through aperture (16) and in the through aperture a hollow screw (8') is placed, which contains a threaded aperture (10) and which is adapted to be screwed through a pedicle into a spinal vertebra (7) body.

8. The device according to claim 6, wherein the segment (1) contains the bearing case (5) in the form of an excavation formed in the segment body (2) with one side open and covered by the fixation washer (13).

9. The device according to claim 8, wherein the spring (4) contains at its free end at least on a part of the circumference enlargement (16), and a groove (17) is formed at the end of the bearing case (5) of the second segment (1') which is more removed from the first segment (1), on which the spring (4) is fixed.

10. The device according to claim 1, wherein the fixing element (3) is a shaped clamp equipped at the ends of arms with a tightening screw (6), and the internal aperture of the fixing element (3) has a form of a cross cut of the vertebral arch (7) in a place between the spinous processus and the pedicle of the vetebra (7).

* * * * *